US00PP21215P2

(12) United States Plant Patent
Bak et al.

(10) Patent No.: US PP21,215 P2
(45) Date of Patent: Aug. 17, 2010

(54) ***GUZMANIA* PLANT NAMED 'ALTO'**

(50) Latin Name: *Guzmania sp.*
Varietal Denomination: ALTO

(75) Inventors: Elly Bak, Rijsenhout (NL); Nicolaas D. M. Steur, Oude Niedorp (NL)

(73) Assignee: Corn. Bak B.V., Assendelft (NL)

( * ) Notice: Subject to any disclaimer, the term of this patent is extended or adjusted under 35 U.S.C. 154(b) by 0 days.

(21) Appl. No.: 12/383,286

(22) Filed: Mar. 23, 2009

(51) Int. Cl.
*A01H 5/00* (2006.01)

(52) U.S. Cl. ..... Plt./371

(58) Field of Classification Search ..... Plt./371
See application file for complete search history.

(56) References Cited

OTHER PUBLICATIONS

European Union—Community Plant Variety Office (CPVO) R-Form, listing application number and filing date for corresponding, CPVO application No. 2008/2572 filed Nov. 17, 2008 (1 page).
Ministry of Agriculture, Forestry and Fisheries of Japan, Notification No. 658, listing application number and filing date information for corresponding Japanese PBR application No. 23699 filed Apr. 24, 2009. (2 pages) (English Translation provided).

*Primary Examiner*—Susan B McCormick Ewoldt
(74) *Attorney, Agent, or Firm*—Foley & Lardner LLP

(57) ABSTRACT

A new and distinct *Guzmania* hybrid plant named 'ALTO' characterized by solid growth habit; funnel-form rosette plant, measuring about 42 cm in height (above the pot when flowering); numerous, yellow-green color foliage, measuring about 25 to 40 cm in length and about 3.0 cm to 4.0 cm in width; superior floral bract production; bracts have a unique greyed-purple inflorescence (RHS 187B); head inflorescence, measuring from about 8 cm in height when flowering commences to about 15 cm in height at maturity, and about 8 cm in diameter; and long-lasting habit.

2 Drawing Sheets

*Guzmania* plant named 'ALTO'

Latin name of the genus and species of the claimed plant

*Guzmania* sp.

Variety denomination

'ALTO'

BACKGROUND OF THE INVENTION

The present invention relates to a new and distinct hybrid cultivar of *Guzmania* plant, botanically known as *Guzmania* sp., of the family Bromeliaceae, and hereinafter referred to as 'ALTO'

*Guzmania* is native to tropical America. *Guzmania* is predominantly epiphytic with a few terrestrial species and is native to the tropics. For the most part, species vary in diameter from 7 or 8 inches to 3 or 4 feet and have rosettes of glossy, smooth-edged leaves. Floral bracts of *Guzmania* frequently have brilliant colors and may last for many months. The range of colors for *Guzmania* is generally from yellow through orange but may also include flame red and red-purple. White or yellow, tubular, three-petalled flowers may also appear on a stem or within the leaf rosette but are usually short-lived. *Guzmania* may be advantageously grown as pot plants for greenhouse or home use. Typically, the plants are shaded from direct sunlight. During the spring to autumn period, the central vase-like part of the leaf rosette is normally filled with water.

The new *Guzmania* 'ALTO' originated from a cross made in a controlled breeding program by the inventors in 1996. The female or seed parent is the *Guzmania lingulata* minor identified by code 84336 (unpatented). The male or pollen parent is the *Guzmania conifera* identified by code 9678530 (unpatented). The new *Guzmania* 'ALTO' was discovered and selected by the inventors in 2000 as a single flowering plant within the progeny of the stated cross in a controlled environment in Assendelft, The Netherlands.

Asexual reproduction of the new *Guzmania* cultivar was first performed by off-shoots beginning in 2001 and then by tissue culture beginning in 2003 in Assendelft, The Netherlands, with first flowering after asexual reproduction occurring in 2008 in Assendelft, The Netherlands. Asexual reproduction of the *Guzmania* 'ALTO' has demonstrated that the combination of characteristics as herein disclosed for the new cultivar are firmly fixed and retained through successive generations of asexual reproduction. The new cultivar reproduces true to type.

Methods for cultivation and crossing of *Guzmania* are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN, Verlag, Paul Parey, Berlin (1986); and Rauh, Werner, BROMELIEN, Verlag Eugen Ulmer, Stuttgart (1981).

BRIEF SUMMARY OF THE INVENTION

The following traits have been repeatedly observed and are determined to be unique characteristics of 'ALTO' which in combination distinguish this *Guzmania* as a new and distinct cultivar:

1. Solid growth habit;
2. Funnel-form rosette plant, measuring about 42 cm in height (above the pot when flowering);
3. Numerous, yellow-green color foliage, measuring about 25 to 40 cm in length and about 3.0 cm to 4.0 cm in width;
4. Superior floral bract production;
5. Bracts have a unique greyed-purple inflorescence (RHS 187B);
6. Head inflorescence, measuring from about 8 cm in height when flowering commences to about 15 cm in height at maturity, and about 8 cm in diameter; and
7. Long-lasting habit.

Plants of the parental cultivars, *Guzmania lingulata minor* identified by code 84336 and *Guzmania conifera* identified by code 9678530 (both unpatented) are no longer available to provide a botanical comparison with the new *Guzmania* hybrid 'ALTO'.

Of the many commercial cultivars known to the present inventors, the most similar in comparison to the new *Guzmania* hybrid 'ALTO' is the *Guzmania* 'TORCH' (patented, U.S. Plant Pat. No. 9,426). Plants of the new hybrid 'ALTO' differ from plants of 'TORCH' primarily in the following characteristics:

1. Plants of 'ALTO' produce head inflorescence which are greyed-purple (closest to RHS 187B) in color and measure at maturity about 15 cm in length and about 8 cm in diameter whereas plants of 'TORCH' produce single inflorescence which are bright red (closest to RHS 44A) in color and measure at maturity about 18 cm in length and about 8 cm in width;
2. Plants of 'ALTO' produce leaves that measure about 25 cm to 40 cm in length and about 3.0 cm to 4.0 cm in width whereas plants of 'TORCH' produce leaves that measure about 37 cm in length and about 5 cm in width; and
3. Plant of 'ALTO' bloom for a whole year about 18 weeks after natural induction or through flowering induction whereas plants of 'TORCH' bloom for a whole year about 16 weeks after natural induction or through flowering treatment.

BRIEF DESCRIPTION OF THE PHOTOGRAPHS

The accompanying photographs illustrate the overall appearance of the new *Guzmania* hybrid 'ALTO' showing the colors as true as is reasonably possible with colored reproductions of this type. Colors in the photographs may differ slightly from the color values cited in the detailed botanical description which accurately describes the color of 'ALTO'.

DETAILED BOTANICAL DESCRIPTION

Figure 1:
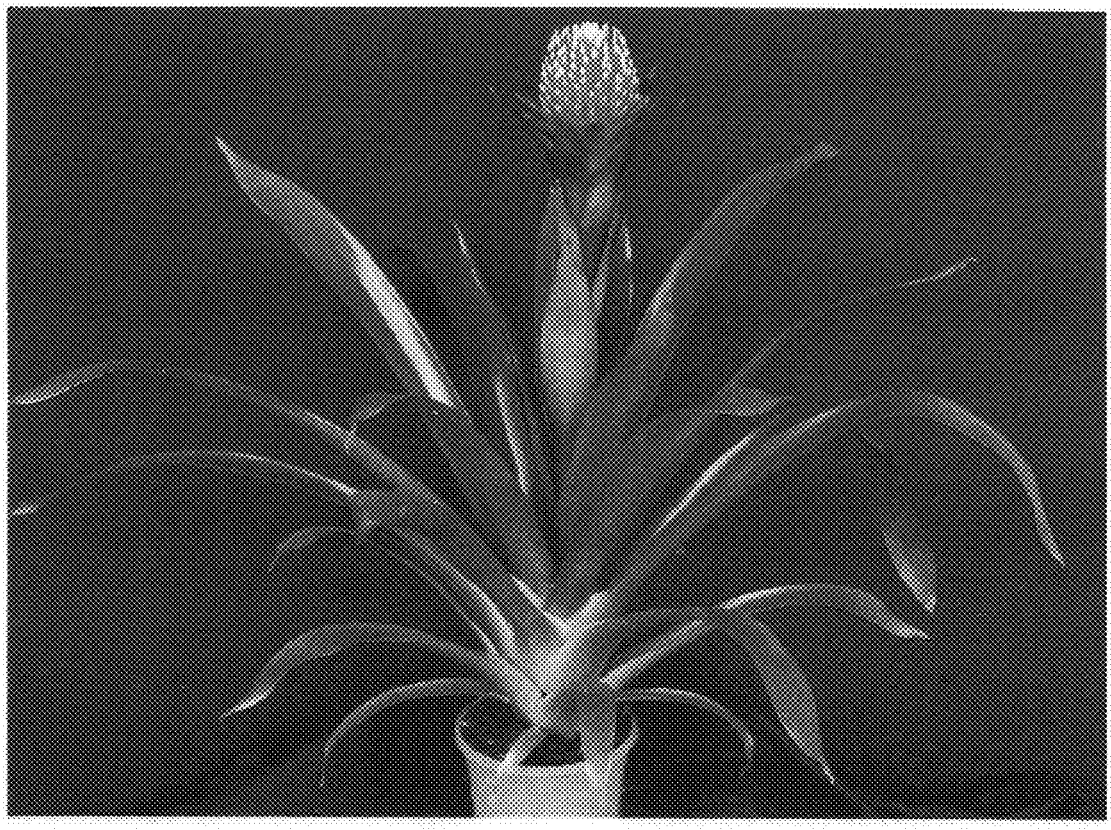
FIG. 1 shows a side view perspective of the primary and top bracts produced by a typical potted, flowering plant of 'ALTO', at 15 months of age from potting size.
Figure 2:
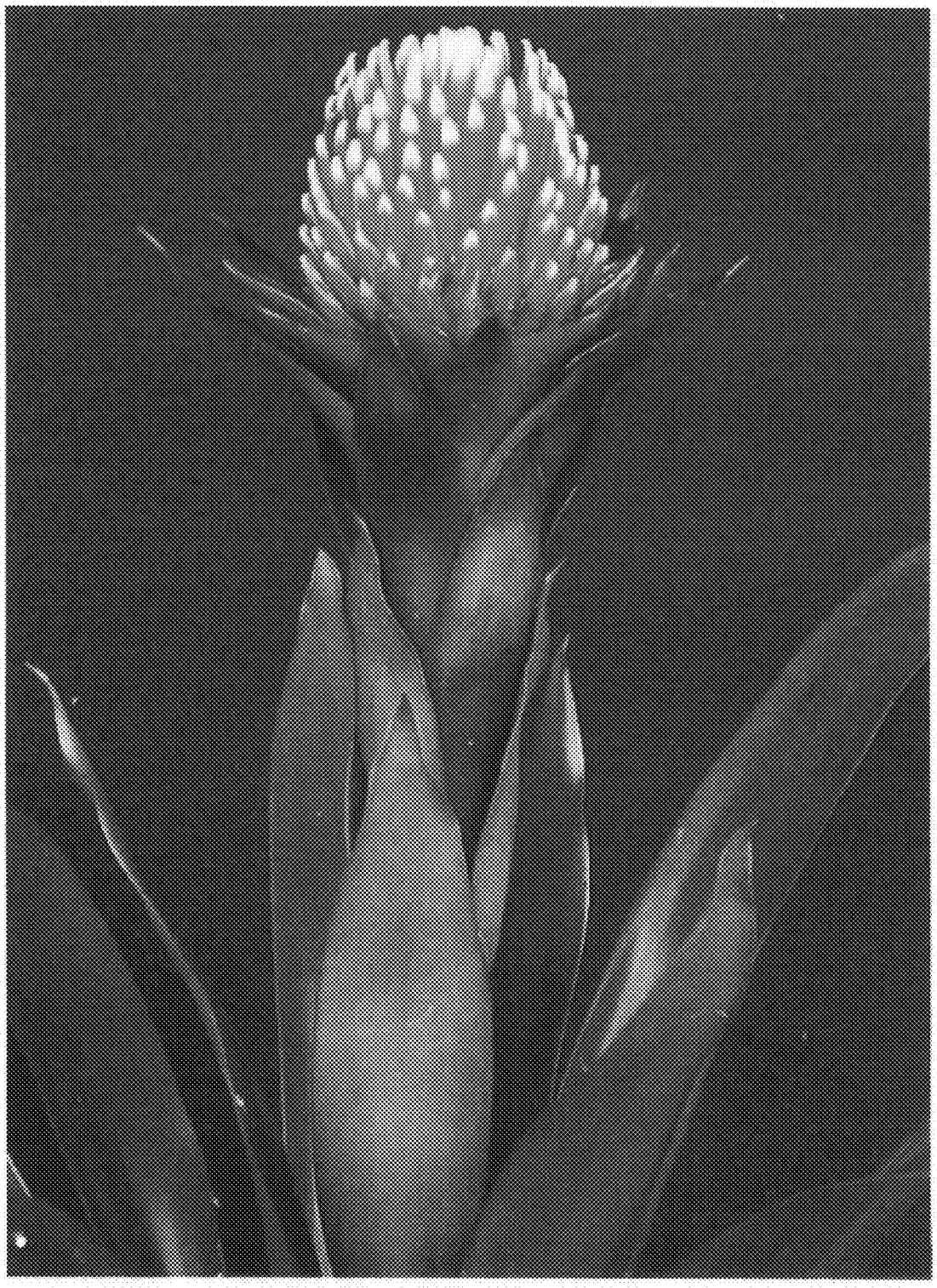
FIG. 2 shows a close-up top view perspective of the inflorescence and top bracts produced by a typical potted, flowering plant of 'ALTO', at 15 months of age from potting size.

'ALTO' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant.

For example, substantial differences in plant height and diameter, number of leaves, can result depending on the size of the plant at the time that flowering is induced by flowering treatment. Since treatment to induce flowering disrupts normal watering and fertilization regimens, flowering treatment of relatively smaller plants adversely affects the growth of the plant.

The aforementioned photographs, together with the following observations, measurements and values describe the new *Guzmania* 'ALTO' as grown in a greenhouse in Assendelft, The Netherlands, under conditions which closely approximate those generally used in commercial practice. Plants of 'ALTO' were grown in a greenhouse with day temperatures ranging from 20° C. to 28° C. and night temperatures ranging from 18° C. to 23° C. No artificial lighting or photoperiodic treatments were conducted, but plants of 'ALTO' are forced into flowering. The following fertilizer is added when growing plants of 'ALTO': 1 part nitrogen, 0.6 parts phosphor, 2 parts Kalium and 0.1 parts magnesium.

Color references are made to the Royal Horticultural Society Colour Chart (RHS), 2001 edition, except where general colors of ordinary significance are used. Color values were taken under daylight conditions in a greenhouse in Assendelft, The Netherlands. The age of the plants of 'ALTO' described is about 18 weeks after flowering treatment.

Classification:

*Botanical.*—*Guzmania* sp.

Parentage:

*Female parent.*—*Guzmania lingulata minor* identified by code 84336 (unpatented).

*Male parent.*—*Guzmania conifera* identified by code 9678530 (unpatented).

Plant:

*General Appearance and Form.*—Height: About 42 cm (when flowering). Width: About 60 cm. Shape: Funnel form rosette.

*Growth habit.*—Stemless.

*Plant vigor.*—Good.

*Flowering season.*—A fully grown plant can flower year round, starting 18 weeks after induction of natural light or through flowering treatment.

*Cold tolerance.*—Frost tender. Temperatures below 5° C. may damage plants.

*Fragrance.*—None.

Foliage:

*Quantity.*—About 22 (depending on the size of the plant).

*Size of Leaf.*—Length: About 25 cm to 40 cm (when flowering). Width: About 3.0 to 4.0 cm.

*Overall shape.*—Linear-lanceolate.

*Apex shape.*—Acute.

*Base shape.*—Strap-like around central axis.

*Margin.*—Entire.

*Texture* (*both surfaces*).—Smooth.

*Orientation.*—Leaf blades arch continuously from base.

*Color.*—Leaf color can vary somewhat depending on growing conditions Mature: Upper surface: Yellow-green, RHS 147A. Under surface: Yellow-green, RHS 147A with anthocyanin. Immature: Upper surface: Yellow-green, RHS 147A. Under surface: Yellow-green, RHS 147A.

*Venation.*—None.

Inflorescence:

*Borne.*—Erect stalks.

*Shape.*—Head.

*Size.*—Length (increases with maturity): From about 8 cm when flowering commences, to 15 cm at maturity. Diameter: About 12 cm.

*Time of bloom.*—A fully grown plant can produce an inflorescence containing about 150 flowers (depending on the size of the plants), and can bloom the whole year starting about 18 weeks after natural induction or through flowering treatment.

*Duration of bloom.*—Each flower blooms one (1) day and the total blooming of the whole inflorescence is about twenty (20) weeks.

*Petals.*—Number: 3 per flower. Length: About 5.0 cm. Width: About 0.5 cm. Overall Shape: Ligulate. Apex Shape: Obtuse. Base Shape: Fused. Color: Upper and Under surfaces: Yellow, RHS 9A.

*Sepals.*—Number: 3 per flower. Length: About 2.0 cm. Width: About 0.5 cm. Overall Shape: Ligulate. Apex Shape: Acute. Base Shape: Fused. Color: Translucent.

Bracts:

*Scape Bracts.*—Quantity: About 12. Arrangement: Alternate. Size: Length: About 31 cm (lowest) to about 12 cm (scape bracts positioned just below the primary bracts). Width: About 3.5 cm. Overall shape: Lanceolate. Apex shape: Acute. Base shape: Fused. Margin: Entire. Texture: Smooth. Color: Upper surface: Greyed-purple, RHS 187B. Under surface: Greyed-purple, RHS 187B.

*Primary Bracts.*—Quantity: About 4. Arrangement: Alternate. Size: Length: About 12 cm (lowest) to about 8 cm (primary bracts become shorter closer to the top of plant). Width: About 3.0 cm. Overall shape: Lanceolate. Apex shape: Acute. Base shape: Fused. Margin: Entire. Texture: Smooth. Color: Upper and Under surfaces: Greyed-purple, RHS 187B.

*Floral bracts.*—Quantity: About 150. Size: Length: About 8 cm (lowest) to about 2 cm (become shorter closer to top of plant). Width: About 1.0 cm. Overall shape: Lanceolate. Apex shape: Obtuse. Base shape: Fused. Margin: Entire. Texture: Smooth. Color: Lower floral bracts: Upper and Under surfaces: Greyed-purple, RHS 187C. Higher floral bracts (closer to top of plant): Upper and Under surfaces: Yellow, RHS 9A.

Reproductive organs:

*Androecium.*—Stamen: Number: 6 per flower. Length: About 2.0 cm. Diameter: About 1.0 mm. Color: Yellow, RHS 8C. Anther: Length: About 0.5 cm. Color: Yellow, (too small to qualify RHS value). Pollen: Amount: Scarce. Color: Yellow, (too small to qualify RHS value).

*Gynoecium.*—Pistil: Number: 1 per flower. Length: About 3.5 cm. Stigma: Shape: 3-parted. Width: About 3.0 mm. Color: Green, (too small to qualify RHS value). Style: Length: About 3.0 cm. Color: Yellow, RHS 8B. Ovary: Position: Superior. Shape: Conical. Length: About 0.5 cm. Diameter: About 0.3 cm. Color: Green, (too small to qualify RHS value).

Seeds/fruit: Sterile hybrid, therefore, no seed or fruit produced.

Disease/pest resistance: No observations made.

Disease/pest susceptibility: No observations made.

We claim:

1. A new and distinct *Guzmania* hybrid plant named 'ALTO', substantially as illustrated and described herein.

* * * * *